United States Patent [19]

Park

[11] Patent Number: 4,491,987
[45] Date of Patent: Jan. 8, 1985

[54] METHOD OF ORTHOPEDIC IMPLANTATION AND IMPLANT PRODUCT

[75] Inventor: Joon B. Park, Clemson, S.C.

[73] Assignee: Clemson University, Clemson, S.C.

[21] Appl. No.: 78,225

[22] Filed: Sep. 24, 1979

[51] Int. Cl.³ .......................... A61F 1/00; A61F 1/24; A61F 5/04
[52] U.S. Cl. ........................................ 3/1.91; 3/1.912; 128/92 C
[58] Field of Search ................................ 3/1.9–1.913; 128/92 R, 92 C, 92 CA

[56] References Cited

U.S. PATENT DOCUMENTS

| | | | |
|---|---|---|---|
| 3,314,420 | 4/1967 | Smith | 128/92 |
| 3,351,504 | 11/1967 | DeHart | |
| 3,609,867 | 10/1971 | Hodosh | 32/10 A |
| 3,663,288 | 5/1972 | Miller | |
| 3,713,860 | 1/1973 | Auskern | 3/1 |
| 3,866,248 | 2/1975 | Kummer | 3/1 |
| 3,879,767 | 4/1975 | Stubstad | 3/1.91 |
| 3,892,649 | 7/1975 | Phillips | 3/1 |
| 3,893,196 | 7/1975 | Hochman | 3/1.91 |
| 3,908,201 | 9/1975 | Jones et al. | 3/1 |
| 3,924,274 | 12/1975 | Heimke et al. | 3/1.91 |
| 3,936,887 | 2/1976 | Hodosh | 3/1 |
| 3,938,198 | 2/1976 | Kahn | 3/1.912 |
| 3,955,012 | 5/1976 | Okamura et al. | 3/1 |
| 3,986,212 | 10/1976 | Sauer | 3/1.91 |
| 3,987,499 | 10/1976 | Scharbach et al. | 3/1.91 |
| 4,064,566 | 12/1977 | Fletcher | 128/92 C X |
| 4,064,567 | 12/1977 | Burnstein et al. | 128/92 CA X |
| 4,065,817 | 1/1978 | Branemark | 3/1.91 |
| 4,171,544 | 10/1979 | Hench et al. | 128/92 C |
| 4,202,055 | 5/1980 | Reiner et al. | 3/1.91 |
| 4,281,420 | 8/1981 | Raab | 3/1.912 |
| 4,283,799 | 8/1981 | Pratt, Jr. et al. | 3/1.913 |

FOREIGN PATENT DOCUMENTS 2444831 9/1975 Fed. Rep. of Germany ......... 3/1.91

OTHER PUBLICATIONS

DeWinn et al., "Mechanical Properties of Bone Cements in vitro and in vivo", Excerpta Medica Amsterdam, American Elsevier Pub. Co. Inc., N.Y., 1974, pp. 1–5.

Primary Examiner—Ronald L. Frinks
Attorney, Agent, or Firm—Wellington M. Manning, Jr.

[57] ABSTRACT

An improved process for orthopedic implantation of a prosthesis where the prosthesis has a polymer coating on substantially the entire surface of same that is to be affixed to the bone by bone cement, the polymer coating being substantially completely polymerized and exhibiting a virtually pore free outer surface. After preparation of the bone cavity, a bone cement, preferably a self-curing acrylic is inserted into the bone cavity, after which the precoated prosthesis is properly positioned therein. The polymeric coating on the prosthesis should be compatible with the bone cement to achieve a chemical bond therebetween. A precoated prosthesis is also disclosed and claimed.

14 Claims, 3 Drawing Figures

METHOD OF ORTHOPEDIC IMPLANTATION AND IMPLANT PRODUCT

BACKGROUND OF THE INVENTION

The present invention relates to orthopedic implantation, particularly implantation of prosthetic devices to repair or replace hard tissue of warm-blooded mammals, e.g., bones and joints of humans and animals which processes utilize a bone cement for fixation of the prosthesis.

Substantial effort has been previously expended in the area of orthopedic implantation of prostheses in both human and animals, attempting to repair or replace a diseased or damaged bone and/or joint associated with the bone. In general, orthopedic implantation of prostheses has been fraught with various problems. Specifically, problems have revolved around adequacy of strength characteristics of the prosthesis as well as the physiological impact and effect of the implant on the patient under the influence of normal body functions, tissue, bone, body fluids and the like.

Ideally, the prosthetic implant should be designed to closely assimilate, as much as possible, the characteristics of the bone and/or joint that the implant is intended to repair and/or replace. In particular, the implant should possess adequate structural strength to undergo compressive stress, flexural stress, and the like imparted thereto during normal body function without reaching the point of failure. In like vein, the implant must be resistant to corrosion and other degradation in vivo and should be virtually inert to body fluids. Further the means for securing the implant within the bone should not adversely affect the surrounding body tissue or create any adverse physiological impact on the body system of the patient.

In order to achieve optimization of implant design, prior techniques have involved the manufacture of implants, or prostheses from various materials, each of which has been engineered to possess one or more of the above requisite characteristics for a prosthesis. Generally, prosthetic implants have been manufactured of various metal alloys, ceramics, polymeric materials, mixtures of polymeric materials with metals and/or ceramics, and the like. Certain prostheses have been manufactured with particular porous coatings, normally polymeric or ceramic in nature, attempting to improve fixation by permitting bone tissue growth within porosities of the porous surface.

One widely accepted implantation technique, particularly for joint replacement, especially total hip arthroplasty, utilizes bone cement, generally an acrylic, that is premixed and placed into a prepared bone cavity in which the implant is to be fixed followed by location of the prosthesis in the bone cement and ambient curing or polymerization of the cement. Though the use of bone cement for orthopedic implantation is a generally accepted procedure, certain problems exist concerning the use of same in the implantation technique, the physiological impact on the surrounding body area, and expected useful life of the implant. Bone cement conventionally includes an acrylic polymeric powder which is pre-mixed with a liquid acrylic monomer system to provide a doughy mass. The doughy mass is inserted into the bone cavity.

Polymerization of the bone cement is exothermic in nature, generating temperatures in vivo in excess of 60° C. which can result in necrosis of surrounding body cells. The monomer system is basically toxic in nature and can interfere with the systemic function of the patient, leading to a decrease in blood pressure, and perhaps in certain circumstances, more serious cardiovascular problems. Normal use of the acrylic bone cement can also lead to further problems. After the doughy cementitious mixture has been placed within the prepared bone cavity, the surgeon only has from about two to five minutes during which the prosthesis may be properly located in the bone cavity surrounded by the bone cement. There is thus very little available time for the surgeon to ensure precise placement of the prosthesis. Additionally, the bone cement shrinks during polymerization, possibly leading to the production of both microscopic and macroscopic gaps along the interface between the prosthesis and the cement and/or the cement and the bone tissue, leading to a possibly inferior implantation. In the event of improper placement of the prosthesis, same cannot be merely replaced after polymerization of the bone cement. Instead it is necessary to forcefully remove the prosthesis, drill out the polymerized bone cement, and re-prepare the bone cavity. Not only is the repeat implantation inconvenient to the patient, but there is always the danger of trauma prompted by the additional reaming of the bone cavity. Further, extensive intermedullary cavity preparation can block bone sinusoids, enhancing the probability of tissue necrosis and fat embolism.

The present invention overcomes or substantially reduces the incidence of the problems set forth above with respect to the use of bone cement for surgical implantation of a prosthesis. While many different techniques are set forth in the prior art concerning implantation by the use of bone cement, as exemplified by the following listed patents, none of the prior art is believed to anticipate or suggest the subject matter of the present invention.

U.S. Pat. No. 3,986,212
U.S. Pat. No. 3,866,248
U.S. Pat. No. 3,609,867
U.S. Pat. No. 4,065,817
U.S. Pat No. 3,987,499
U.S. Pat. No. 3,936,887
U.S. Pat. No. 3,314,420
U.S. Pat. No. 3,955,012
U.S. Pat. No. 3,677,795
U.S. Pat. No. 3,924,274
U.S. Pat. No. 3,713,860
U.S. Pat. No. 3,892,649
U.S. Pat. No. 3,663,288
U.S. Pat. No. 3,908,201

SUMMARY OF THE INVENTION

It is an object of the present invention to provide an improved prosthesis for surgical implantation with bone cement for the repair of hard tissue in warm-blooded mammals.

Another object of the present invention is to provide an improved method ,f surgical implantation of prostheses utilizing bone cement to fix the prosthesis in place.

Yet another object of the present invention is to provide an improved method of orthopedic implantation utilizing bone cement to secure a prosthesis in place, which technique reduces the exotherm, reduces the incidence of toxic substances in the body and improves the interfacial bond between the prosthesis and the bone tissue to which it is affixed.

Still further another object of the present invention is to provide an implantable prosthesis, a substantial portion of which is precoated with polymer layer that is compatible with bone cement utilized during surgical implantation of the prosthesis.

Generally speaking, the improved method of orthopedic implantation according to the present invention comprises the steps of providing a prosthetic implant, said implant having a polymer coating over substantially the entire surface that is to be immobilized by a bone cement composition within the bone cavity, said coating having been substantially completely polymerized under appropriate temperature and pressure conditions to achieve a substantially pore free surface, said polymer being compatible with said bone cement to be used during implantation; preparing the bone of patient to provide a cavity to receive the prosthetic implant and a supply of bone cement; inserting a supply of bone cement into the prepared bone area; contacting the polymer coating on the surface of the prosthetic implant with a monomeric material compatible with the coating and the bone cement; properly positioning the coated portion of the implant in the bone cavity, within the bone cement; and curing the bone cement.

More specifically, the method of orthopedic implantation according to the present invention utilizes a particular prosthetic implant, on which substantially the entire surface of same which designed to be contacted by bone cement during implantation, has received a precoat of a polymeric composition that is compatible with the bone cement to achieve a structurally sound bond therebetween. The surface of the prosthesis to receive the polymer coating should be pretreated immediately prior to application of the coating to roughen or otherwise prepare the surface to achieve a structurally sound bond at the prosthesis coating interface. After application of the coating preferably with a bone cement mixture of the type to be utilized during implantation, the coating is polymerized under adequate temperature and pressure conditions to remove any bubbles and yield a virtually pore free outer surface. While the thickness of the pre-coat should be adequate to insure a good cement/cement bond, the greater the thickness of the pre-coat, the lesser amount of bone cement needed during implantation. The maximum thickness of the pre-coat is controlled only by the size of the bone cavity to be prepared, realizing that the polymer pre-coat should be entirely covered with new bone cement during implantation.

Prior to implantation, the cancellous bone is reamed to the desired diameter and length to receive the pre-coated prosthesis and an appropriate quantity of bone cement, and is cleaned to remove particulate matter therefrom. A predetermined quantity of bone cement is then mixed and kneaded to achieve a doughy consistency, after which same is placed into the cancellous bone cavity with adequate force to impregnate porosities of the bone tissue. The precoated implant is then properly located within the bone cavity, surrounded by the cementitious composition. Thereafter, the cementitious composition is permited to cure at ambient temperature. A rapid initial cure, or polymerization, takes place, and after an appropriate period of time, the incision is closed. Complete polymerization of conventionally used bone cement occurs in vivo over the span of approximately 30 to 40 days.

According to the present invention, metallic prostheses are preferred, and without limitation include cobalt-chromium alloys, titanium and its alloys, platinum metals, tantalum, stainless steels and the like. These general types of metals have enjoyed wide acceptance due to the ease of fabrication of high quality prostheses from same, good physical characteristics, and the excellent resistance to corrosion in vivo. Insofar as the present invention is concerned, however, any type of prosthetic implant may be utilized so long as the requisite structural qualities are present, and bone cement will suitably bond thereto.

Bone cement provides not only the mechanism of attachment of the implant to the bone, but also acts as a shock absorber because of its viscoelastic characteristics. In fact, when utilizing a precoated prosthesis according to the teachings of the present invention, a rigidity gradient is realized across a cross section of the implant, precoat layer, bone cement, and bone tissue whereby improved shock absorbency is realized, leading to better postoperative results.

Any bone cement composition may be utilized according to teachings of the present invention so long as same is compatible with the body system of the patient and will bond adequately to the polymer precoat on the prosthesis. In general, acrylic type bone cements are preferred, which normally are two component systems. Polymer and/or copolymer, such as polymethyl methacrylate and methyl methacrylate-styrene copolymer are provided in powder form, with barium sulfate or some other appropriate material possibly being included to render the cement radio-opaque. The polymeric powder is mixed with a liquid monomer, methyl methacrylate for example, which generally also includes initiators and inhibitors such as N, N-dimethyl-p-toluidine and hydroquinone. The toluidine compound is added to accelerate the decomposition of peroxides and thus promote polymerization while the hydroquinone is added to prevent premature polymerization of the monomer. The cementitious composition components are sterilized prior to use to permit in vivo use of same without undue adverse physiological side effects.

DESCRIPTION OF THE PREFERRED EMBODIMENTS

Figure 1:
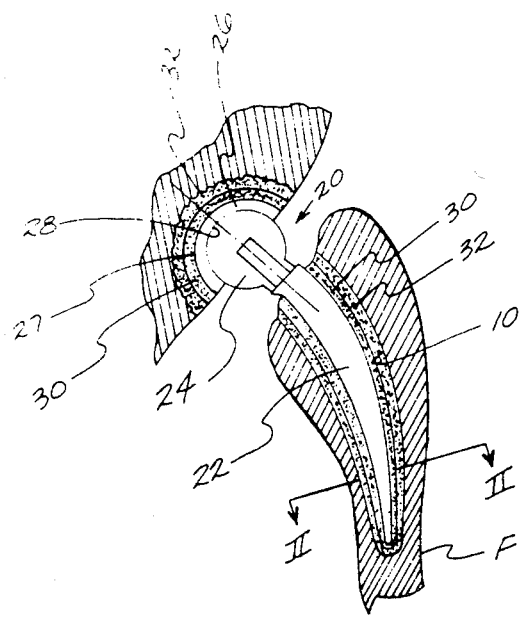
FIG. 1 is a partial vertical cross sectional view of a total hip implant, illustrating the present invention.

The present invention relates to the orthopedic implantation of prostheses utilizing bone cement as a fixative for the implant. The prosthesis to be implanted has a coating thereon of polymeric material that is compatible with the bone cement to be employed during implantation whereby a strong interfacial bond may be achieved between the bone cement and the polymer coating. In a preferred embodiment, the prosthetic precoat is prepared from bone cement of the same composition that is to be used during the operative implantation procedure. The polymer precoat on the prosthesis should have been substantially completely polymerized under proper temperature and pressure conditions to yield a virtually pore free outer surface, and obviously must form a strong bond with the prosthesis around which is resides. The polymeric precoat should be applied to substantially the entire surface of the prosthesis that is normally designed for immobilized fixation and which is not intended for relative movement with respect to the bone or a further portion of the prosthesis. A femoral prosthesis, for example, would be precoated along the stem while the portion of same to be received in the acetabulum, i.e., the ball would not. In like vein, should a prosthetic acetabular cup be utilized, the exterior of same would be precoated while the cup portion to receive the femoral head or ball of the prosthesis would not. In some circumstances, a prosthesis may have a polymeric surface, which in turn would be precoated as set forth herein.

Particular materials from which the prosthesis is manufactured are not critical insofar as the present invention is concerned so long as the prosthesis possesses the requisite strength characteristics and will form an adequate bond with the polymer precoat. Metal alloys such as stainless steels, titanium and cobalt-chromium alloys are, however, preferred. The prosthesis may, however, be fabricated from a combination of metal alloy and polymers such as high density polyethylene, polytetrafluorethylene and the like. Prior to applying the coating to the prosthesis, the portion of the surface of the prosthesis to receive the coating is preferably pretreated to provide a fresh and/or roughened surface. Pretreatment of the prosthesis to prepare the surface is exemplified by sandblasting and acid etching, and should preferably be conducted immediately prior to the precoat operation.

Precoating of the prosthesis may be conducted in any fashion that will permit the attainment of a uniform, pore free surface where substantially complete polymerization of the coating has taken place. In fact, a prosthesis that has previously been manufactured with a porous outer coating and not designed for use with bone cement may be precoated according to teachings of the present invention to achieve an improved implantation. Utilizing a polymer precoat according to the present invention with substantially complete polymerization of the precoat in vitro, an improved interfacial bond between the prosthesis and the bone cement is achieved. In a most preferred embodiment of the present invention, the prosthesis is manufactured from a chromium cobalt alloy such as Vitallium. Portions of the prosthesis which that are to receive the bone cement precoat are preferably pretreated with sulfuric acid, sandblasted or the like to prepare the fresh, roughened surface. Bone cement is then placed therearound in proper quantity and the composite is treated under temperature and pressure adequate to realize substantially complete polymerization of the bone cement. A pressure of the magnitude of approximately 1.5 mega Paschals is normally adequate to achieve the desired polymerization at ambient temperature. Thickness of the coating will vary depending upon the size of the prosthesis, and is determinative of the amount of bone cement that is necessary during the operative procedure. During implantation, adequate void space should be available in the bone cavity to receive the implant and to enable fresh bone cement to totally surround the prosthesis along its length. The precoat polymer may also be reinforced with fibrous materials for greater strength, preferably fibers of like material as the bone cement, e.g., acrylic fibers.

Much has been reported about the use of bone cement for fixation of a prosthesis during an operative implantation procedure. During polymerization of methyl methacrylate monomer of the bone cement, present in both commercially approved versions of same in the United States, hoop stress develops in the bone cement due to shrinkage of the polymer. Depending upon the particular polymer and amount of same utilized, hoop stress in the polymer can be of sufficient magnitude to create cracks in the bone cement layer and/or to create microscopic and macroscopic separations between the bone cement and the cancellous bone. The degree of shrinkage of the polymer is proportional to the amount of new bone cement used during the operative procedure. Utilizing techniques of the present invention where a precoated prosthesis is utilized, a lesser amount of new bone cement is required, thus reducing polymer shrinkage and therefore hoop stress in the polymerized bone cement.

One commercially approved self-curing, bone cement composition, Surgical Simplex ® P, manufactured by Howmedica, Inc., Rutherford, N.J., is a two component system which includes a powder, 16.7 weight percent polymethyl methacrylate and 83.3 weight percent methyl methacrylate-styrene copolymer, and a liquid, 97.4 volume percent of methyl methacrylate monomer, 2.6 volume percent of N, N-dimethyl-p-toluidine and 75 plus or minus 15 parts per million of hydroquinone. If radio opacity is desirable for the bone cement, the powder component includes 15 weight percent polymethyl methacrylate, 75 weight percent methyl methacrylate-styrene copolymer and 10 weight percent of barium sulfate. A further commercially approved self-curing bone cement is manufactured by Zimmer U.S.A., Warsaw, Ind. and is likewise a two component system. The powder includes 99.25 weight percent of polymethyl methacrylate and 0.75 weight percent of benzoyl peroxide or, if radio-opacity is desired, 89.25 weight percent of polymethyl methacrylate, 10 weight percent of barium sulfate, and 0.75 weight percent of benzoyl peroxide. The liquid component includes 97.25 volume percent of methyl methacrylate monomer, 2.75 volume percent of N, N-dimethyl-p-toluidine and 75 plus or minus 10 parts per million of hydroquinone. While the two bone cements set forth above are the only two presently approved by the Food and Drug Administration for use in the United States, obviously other chemical compositions could likewise be suitable and should be considered to be within the purview of the present invention.

For implantation use, the two components of the bone cement are mixed and kneaded until a doughy consistency is obtained. A mixing-kneading time of at least four minutes is recommended to reduce the amount of free monomer that can be absorbed into the patient's bloodstream. The doughy cement is immediately forced into the bone cavity that has been prepared to receive the prosthesis. In the sense of cancellous bone structure, the bone cement is forced into the cavity with adequate pressure to place the doughy mixture within the interstices of the bone to provide a good physical interlock between the bone cement and the bone after curing of the bone cement. Subsequent to placement of the doughy mixture of bone cement composition within the prepared bone cavity, the precoated prosthesis is wiped along the precoated surface of same with methyl methacrylate monomer and the prosthesis is then properly located within the bone cavity where it will become firmly implanted in the bone cement. Wiping of the polymer precoat with methyl methacrylate monomer will dissolve some of the surface of the polymer and thus foster a good interfacial bond between the old cement and the new cement.

Polymerization of the bone cement composition is exothermic and generates in vivo temperatures of around 60° C., which can lead to necrosis of the surrounding bone tissue. Likewise, methyl methacrylate monomer is toxic substance and adversely affects the systemic system of the patient. According to the techniques of the present invention utilizing a precoated prosthesis, a lesser amount of new bone cement is employed during the surgical procedure. The exotherm of the reaction is thus lessened, decreasing the probability of necrosis and the lesser amount of toxic monomer decreases the probability of systemic interference.

Under normal conditions, once the components of the bone cement are mixed and forced into the prepared bone cavity, polymerization has begun and a state of curing of the polymer is reached in approximately two to five minutes where further manipulation of the implant becomes difficult. Hence, there is very little time during the operative procedure for proper positioning and location of the prosthesis within the bone cavity. Moreover, after positioning of the prosthesis and sufficient polymerization of the bone cement to secure the prosthesis, subsequent removal of the prosthesis for repositioning or replacement requires a further reaming of the bone cavity to remove the old polymerized bone cement. Since the actual reaming of the bone to provide the implant cavity may possibly damage the bone tissue, proper initial location of the prosthesis is particularly important. Should the prosthesis make contact with the inner surface of the bone cavity without a bone cement buffer therebetween, later physical movement is subject to cause abrasion of the bone. Abraded particulate bone matter becomes free within the bone cavity, leading to early failure of the implant.

A precoated prosthesis according to the present invention avoids the abrasion problem since there is no possibility malpositioning of the prosthesis to cause direct contact between the inner wall of the bone cavity and the implant. The precoated implant according to the present invention is thus considered to have an "autocentering" capability. Additionally, as will be pointed out hereinafter, a greatly improved bond strength is realized between the old cement and the new cement, i.e., the precoat polymer and the polymerization mass that is utilized during implantation. Moreover, there is, by virtue of the precoat polymer, a shock gradient that assists in distributing the compressive load placed on the implanted bone. It has been known that the bone cement in general provides such a gradient in distributing stresses from the implant to the bone. When, however, a precoat polymer is utilized there is yet a further shock gradient level to permit a more gradual transmission of shock from the implant to the bone tissue, leading to a longer implant life.

Figure 2:
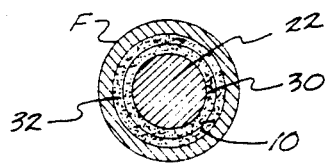
FIG. 2 is a horizontal cross section taken along a line II—II of FIG. 1 to further illustrate the present invention.

Making reference to the Figures, a prosthesis and the procedures of implantation according to the present invention will now be described in greater detail. Utilizing, by way of example, a total hip implantation, as schematically illustrated in FIGS. 1 and 2, the femur F has been reamed out to prepare a cavity 10 in which the prosthesis generally indicated as 20 is to be implanted. The hip prosthesis includes a stem 22 having a ball 24 at a proximal end of same. Ball 24 resides in a prosthetic socket 26 that is located at the acetabular socket and cemented therein. According to techniques of the present invention, stem 22 of the femoral prosthesis 20 has a polymer coating 30 therealong, coating 30 extending totally around stem 22 and along the entire length of same received within femoral cavity 10. In like fashion, the outer surface 27 of the acetabular socket 26 is provided with a polymer precoat 30, the inner surface 28 of same being uncoated as well as the ball 24. Both stem 22 and socket 26 are secured in their respective cavities by a new bone cement mass 32. In a most preferred technique, a two component bone cement system is mixed to a doughy consistency and placed in a mold, after which the prosthesis with a roughened surface is placed therein and maintained under adequate temperature and pressure to substantially completely polymerize the bone cement precoat. The polymeric precoat 30 should be substantially completely polymerized to a point of achieving a substantially pore free outer surface.

After reaming out the bone cavity 10, and premixing the bone cement composition to a doughy consistency, the doughy cement mixture is placed into bone cavity 10 with sufficient force that the doughy cement is forced into the interstices of the cancellous bone to provide a good mechanical interlock following polymerization of the bone cement. The prosthesis having the polymer precoat thereon is then quickly properly located within the bone cavity, being surrounded by the fresh bone cement 32. As mentioned above, due to the precoat, there is "auto-centering" of the prosthesis such that there is no direct contact between the inner surface of the bone that defines cavity 10 and the stem 22 or outer surface 27 of socket 26 of prosthesis 20. Additionally, since the precoat takes up additional space, a lesser amount of fresh or new bone cement composition is needed to fill cavity 10 whereby the exotherm from the polymerization reaction is less, less monomer is used, and there is less shrinkage of the polymer, all of which add to a better fixation and longer life of the implant.

Figure 3:
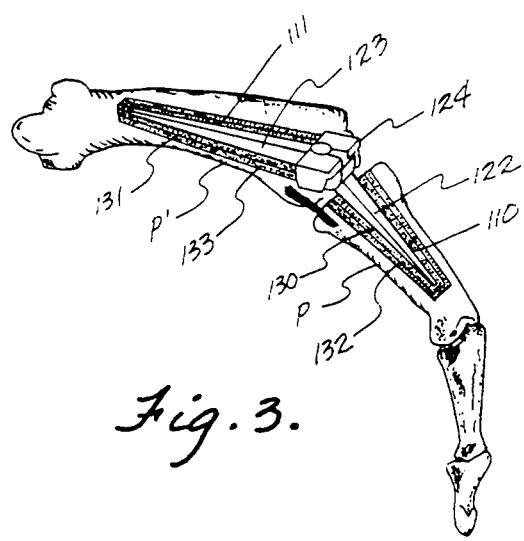
FIG. 3 is a partial cross sectional view of a finger joint having a prosthesis implanted therein to illustrate applicability of the present invention to other prosthetic devices.

An implanted finger joint prosthesis is illustrated in FIG. 3 where the prosthesis includes a pair of stems 122 and 123 that are hingedly connected at a mechanical joint 124, joint 124 being located at the normal joint between adjacent phalanges P and P' of the digit. Stems 122 and 123 extend outwardly from joint 124 in opposite directions and are implanted within cavities 110 and 111 respectively of phalanges P, P'. Stems 122 and 123 of the finger prosthesis are precoated with a polymeric material 130, 131 preferably bone cement, as indicated above with respect to the hip prosthesis, with fresh bone cement composition 132, 133 being provided in the cavities 110 and 111 of the phalanges P, P' to receive the prosthesis therein. For all practical purposes, the finger prosthesis having the hinge portion 124 is the same as set forth above with respect to the hip prosthesis from the standpoint of the present invention, that is, the precoats 130, 131 are applied along substantially the entire surfaces of the prosthesis that are to be secured within phalange cavities 110, 111.

Making reference to the following examples, the present invention may be better understood.

EXAMPLE 1

To ascertain the strength qualities of various implants with respect to the present invention, four rods (0.49 centimeters in diameter × 13 centimeters long) were manufactured from type 304 stainless steel stock. Two of the rods were polished and two were sandblasted to provide a roughened surface. All four rods were then coated with acrylic bone cement (radiolucent Surgical Simplex® P, manufactured by Howmedica, Inc.), identified above. The rods were coated with the acrylic bone cement in a mold, and were left to cure for several days, the resultant coating having a thickness of approximately 2 millimeters. After curing, serial sections were made using a diamond saw and constant cooling with tap water, subsequent to which push out mechanical tests were performed on the discs, using an Instron machine at a cross-head speed of 0.025 centimeters per minute. The polished rods were determined to have the maximum sheer stress from the push out test of 0.50 plus or minus 0.21 mega Paschal (MPa) while the sandblasted rod exhibited a maximum sheer stress of 6.84 plus or minus 0.94 MPa, thus demonstrating the greater interfacial implant-precoat maximum stress with the sandblasted rods.

EXAMPLE 2

Four types of implants were utilized to determine strength characteristics after implantation into canine femurs in vitro, particularly to evaluate the interfacial sheer strength in addition to the bench test. The four types of implants included an actual canine femoral prosthesis (Richards Manufacturing Co.), a polished steel rod (0.49 centimeters diameter × 13 centimeters long) with and without precoating, and a sandblasted steel rod precoated with Surgical Simplex® P bone cement as described in Example 1. The femoral heads of freshly excised canine femora were removed with a hacksaw and the femoral medullary canals were reamed and cleaned using bottle brushes and saline solution. Surgical Simplex® P bone cement was then pumped into the medullary canals with a caulking gun, after which the implants were immediately inserted. After curing for three hours at room temperature, the femora were wrapped in towels moistened with Ringer's solution and refrigerated overnight. The entire femora with implants were sectioned in horizontal slices after which the interfacial sheer strengths were determined. Results are tabulated in Table I.

TABLE I

Summary of Push-out Tests after Implantation in Canine Femurs In Vitro

| Type of Interface | Number of Samples | Maximum Sheer Stress (MPa) | Load Displacement (kN-m/m) |
|---|---|---|---|
| Bone/Cement | 15 | 1.17 ± 0.69 | 1.43 ± 1.07 |
| Rod*/Cement | 9 | 3.94 ± 0.78 | 7.10 ± 2.58 |
| Cement/Cement | 3 | 23.40 ± 1.59 | 48.55 ± 24.09 |

*includes polished and sand-blasted rods. The data analyzed revealed that the differences between the interfaces are statistically significant (p<0.01).

Referring to Table I, it is noted that the maximum sheer stress was appreciably greater for the cement/cement interface, i.e., the precoated implant. It was further noted making reference to the serial cross sections of the femora that the rods with precoating were forced to the center of the bone cavity due to the actual presence of the bone cement precoat.

EXAMPLE 3

Example 2 was repeated with the exception that the tests were conducted in vivo, utilizing the intermedullary cavities of the femora of large, random source dogs, employing an aseptic surgical technique. One femur was implanted with a precoated rod implant while the other was implanted with an uncoated rod implant and was used as a control. The implant period was three weeks, and during the first postoperative week, the animal movement was restricted to a minimum by confining the animal to a cage. Upon recuperation, the animal was returned to its outside kennel. Mechanical tests for the in vivo experiments were conducted in similar fashion to those of the in vitro with results tabulated in Table II.

TABLE II

Summary of Push-out Tests for Bone/Cement Interfaces in Canine Femurs In Vivo after 3 Weeks of Implantation

| Type of Implant | Number of Samples | Maximum Shear Stress (MPa) | Load Displacement (kN-m/m) |
|---|---|---|---|
| Uncoated Rod Implant | 8 | 1.65 ± 0.82 | 1.37 ± 6.25 |
| Precoated Rod Implant | 8 | 1.71 ± 0.83 | 1.84 ± 8.38 |

Having described the present invention in detail, it is obvious that one skilled in the art will be able to make variations and modifications thereto without departing from the scope of the invention. Accordingly, the scope of the present invention should be determined only by the claims appended hereto.

That which is claimed is:

1. An orthopedic prosthesis for implantation within a warm blooded mammal with a bone cement composition, said prosthesis comprising a base material structurally defined as to shape and strength to assimilate a portion of hard mammal tissue, said prosthesis having a polymer coating thereabout for contact with bone cement during implantation and having an enlarged surface area therebeneath to provide an improved bond between said prosthesis and said polymer coating, said polymer coating being uniform about said prosthesis, and being up to about 2 millimeters thick, being substantially completely polymerized, having a substantially pore free outer surface, and being compatible with said bone cement composition used during implantation to achieve a chemical bond therebetween.

2. The prosthesis as defined in claim 1 wherein the prosthesis is constructed at least in part from a metal alloy, and the surface of same to be coated was sandblasted.

3. The prosthesis as defined in claim 1 wherein the prosthesis is constructed at least in part from a metal alloy, and the surface of same to be coated was etched with acid.

4. The prosthesis as defined in claim 1 wherein the polymer coating on the prosthesis is of like composition as a bone cement used during the surgical implantation of the prosthesis.

5. The prosthesis as defined in claim 4 wherein the polymer composition is polymethyl methacrylate.

6. The prosthesis as defined in claim 4 wherein the polymer coating is a polymethylmethacrylate-methylmethacrylate-styrene copolymer.

7. A method of orthopedic implantation of a prosthesis with a bone cement composition comprising the steps of:
(a) providing a prosthesis to be implanted, said prosthesis having a uniform, substantially completely polymerized polymer coating thereabout forming a precoated area to be bonded to said bone cement during implantation, said polymer coating being up to about 2 millimeters thick, having a pore free outer surface and being chemically bondable with said bone cement;

(b) preparing the area of the patient to receive the prosthesis adequate to receive the prosthesis and a quantity of bone cement composition;

(c) inserting a quantity of said bone cement composition into the prepared area, adequate to at least completely surround said polymer coating;

(d) immediately positioning said prosthesis in the prepared area such that said bone cement composition at least completely surrounds said precoated area of said prosthesis; and (e) permitting said bone cement composition to cure whereby improved fixation of said prosthesis results.

8. The method as defined in claim 7 wherein the polymer coating and the bone cement composition comprise acrylics.

9. The method as defined in claim 8 wherein acrylic comprises polymethylmethacrylate.

10. The method as defined in claim 7 wherein the bone cement composition comprises a mixture of an acrylic polymer, an acrylic monomer, and a catalyst.

11. The method as defined in claim 10 wherein the acrylic polymer is polymethylmethacrylate and the acrylic monomer is methylmethacrylate.

12. The method as defined in claim 10 wherein the acrylic polymer is a mixture of polymethylmethacrylate and methylmethacrylate-styrene copolymer and the acrylic monomer is methylmethacrylate.

13. The method as defined in claim 10 wherein the bone cement composition further includes an ingredient to render same radio opaque.

14. The method as defined in claim 13 wherein the ingredient is barium sulfate.

* * * * *